United States Patent [19]

Mazanek et al.

[11] 4,101,569

[45] Jul. 18, 1978

[54] PROCESS FOR THE PREPARATION OF 4,4'-DINITRODIPHENYL CARBONATE

[75] Inventors: Jan Mazanek; Johannes Blahak; Dieter Arlt, all of Cologne, Fed. Rep. of Germany

[73] Assignee: Bayer Aktiengesellschaft, Leverkusen, Fed. Rep. of Germany

[21] Appl. No.: 735,715

[22] Filed: Oct. 26, 1976

[30] Foreign Application Priority Data

Nov. 3, 1975 [DE] Fed. Rep. of Germany ....... 2549036

[51] Int. Cl.² .............................................. C07C 68/06
[52] U.S. Cl. .................................................... 260/463
[58] Field of Search ......................................... 260/463

[56] References Cited

U.S. PATENT DOCUMENTS

| 2,985,688 | 5/1961 | Mersch et al. | 260/463 |
| 3,642,866 | 2/1972 | Witt et al. | 260/463 |
| 3,715,323 | 2/1973 | Crivello | 260/463 |

OTHER PUBLICATIONS

Recueil des Travaux Chemiques, 36, 52 (1916).
Ibid, 40, 510, 512 (1921).

*Primary Examiner*—Joseph Paul Brust
*Assistant Examiner*—Molly C. Eakin
*Attorney, Agent, or Firm*—Burgess, Dinklage & Sprung

[57] ABSTRACT

A process for preparing 4,4'-dinitro-diphenyl carbonate which comprises adding to a sulfuric acid solution of diphenyl carbonate maintained at a temperature between $-40$ and $+40°$ C a nitric acid in a stoichiometric or slight stoichiometric excess.

8 Claims, No Drawings

PROCESS FOR THE PREPARATION OF 4,4'-DINITRODIPHENYL CARBONATE

The invention relates to a process for the preparation of 4,4'-dinitro-diphenyl carbonate by nitration of diphenyl carbonate.

The nitration of diphenyl carbonate has been known for a long time; however, nitration under vigorous conditions leads direct to di-(2,4-dinitrophenyl) carbonate (J. pr. [2] 4, 407 (1870)). It is indeed true that it is possible, under certain conditions, to achieve a nitration to 4,4'-dinitrodiphenyl carbonate (R. 36, 52 (1916)), but the resulting nitration product consists to the extent of only about 80% of 4,4'-dinitro-diphenyl carbonate, whilst 2,2'-dinitro- and 2,4'-dinitro-diphenyl carbonate, in a ratio of about 1:20, make up the remainder. Accordingly, when the nitration product is saponified at most about 90% of p-nitrophenol as well as 10% of o-nitrophenol are obtained (R.40, 510, 512 (1921)). In general, however, and especially at a higher temperature, significant amounts of more highly nitrated by-products are formed during the nitration.

If substantially selective nitration of diphenyl carbonate to 4,4'-dinitro-diphenyl carbonate could be carried out, the saponification of this product would provide a simple process for the preparation of p-nitrophenol with which an unavoidable yield of o-nitrophenol, such as arises when p-nitrophenol is prepared according to the state of the art, would be largely eliminated.

It has now been found, surprisingly, that 4,4'-dinitrodiphenyl carbonate can be obtained in very good yield and in high purity by nitrating diphenyl carbonate when nitric acid is added, in the stoichiometrically required amount or in a slight excess, to a sulphuric acid solution of diphenyl carbonate in the temperature range from −40 to 40° C.

It is essential to the invention that diphenyl carbonate is present in a sulphuric acid solution and that nitric acid is only then added in the stoichiometrically required amount or in a slight excess, in which case the excess is to be kept as small as possible.

Further essential factors for carrying out the process according to the invention are that the reaction is carried out at a low temperature, with not too high a concentration of diphenyl carbonate in the sulphuric acid solution and with a high concentration of sulphuric acid in the sulphuric acid solution, that is to say with highly concentrated sulphuric acid which has only a low water content. Sulphuric acid is understood as $H_2SO_4$ itself and its aqueous solutions.

The three last-mentioned features of the process according to the invention are interdependent. For example, one can obtain the same result at very low temperatures and with a higher concentration of diphenyl carbonate as at a higher temperature and with a lower concentration of diphenyl carbonate in the sulphuric acid solution. One can also compensate for a lower concentration of sulphuric acid by a lower reaction temperature and/or a lower concentration of diphenyl carbonate in the sulphuric acid solution. One can advantageously optimise the process according to the invention in respect of the sulphuric acid concentration, concentration of diphenyl carbonate in the sulphuric acid solution and the temperature parameters in accordance with given conditions and for this purpose only a few determinations are necessary.

On the other hand, it is essential to keep the excess of nitric acid over the stoichiometrically required amount as small as possible. It is generally not possible to compensate a larger excess by appropriate choice of the other parameters and this leads to further nitration of the desired reaction product and to a reduction in the yield due to the increased formation of by-products.

In general, sulphuric acid which contains from 80 to 100, and preferably 88 to 100, % by weight of $H_2SO_4$ (remainder water) is used to prepare the sulphuric acid solution of diphenyl carbonate. The commercially available, approximately 96% strength sulphuric acid is appropriately used.

In a particular process variant, one can use a mixture of sulphuric acid and organic solvents which are inert towards sulphuric acid.

In general, in this case, sulphuric acid which contains from about 80, and preferably about 88, to 100% of $H_2SO_4$ is used; the inert organic solvent can be used in a ratio of 1:30 to 30:1, relative to the volume of the sulphuric acid.

In general, the amount of the organic solvent to be used depends on its nature; the amount which is appropriate in a particular case can easily be determined by a few preliminary experiments.

Examples of such solvents which may be mentioned are: halogenoalkanes, such as methylene chloride, carbon tetrachloride and dichloroethane, aromatic nitrohydrocarbons, such as nitrobenzene and nitrotoluene, and lower aliphatic carboxylic acids and their anhydrides, such as formic acid, acetic acid, propionic acid and acetic anhydride.

It is, of course, also possible to use mixtures of inert organic solvents.

The concentration of diphenyl carbonate in the sulphuric acid solution is generally about 2 to 40, and preferably 3 to 25, % (weight/volume). As already mentioned, the concentration can be varied within this range in accordance with the chosen reaction temperature and sulphuric acid concentration.

Nitric acid which contains 10 to 100% by weight of $HNO_3$ (remainder water) can be used as the nitric acid. Appropriately, however, concentrated nitric acid which contains from 65 to 98% by weight of $HNO_3$, and especially 98% strength by weight nitric acid is used.

In order to achieve complete nitration in accordance with the reaction equation

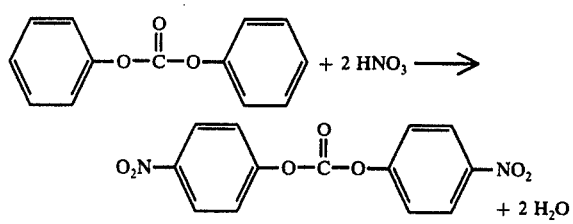

it is, of course, necessary to employ at least the stoichiometric amount of 2 mols of $HNO_3$ per mol of diphenyl carbonate. The use of a small excess of $HNO_3$ is generally advantageous, whilst a larger excess leads to further nitration of the desired reaction product. In general, an excess of up to about 10 mol % has been found to be harmless; preferably, $HNO_3$ is employed in an excess of about 2 to 5 mol %.

As is explained further below, the sulphuric acid and any inert organic solvent employed can be recovered and used again. The small amount of HNO₃ which may still be present in these recovered compounds is not harmful although it is indeed an essential feature of the process according to the invention that a sulphuric acid solution of diphenyl carbonate is first prepared and only then is the nitric acid for the nitration of diphenyl carbonate added.

The nitration can indeed be carried out in the temperature range from −40° C to 40° C, but it is appropriate to carry out the reaction in the temperature range from −20° to 30° C, and especially of −15 to 10° C.

The process according to the invention is simple to carry out. Diphenyl carbonate is dissolved in the sulphuric acid used or in the mixture used. The solution is then brought to the reaction temperature and the desired amount of nitric acid is added at the rate at which it is consumed, provision being made, in the customary manner, to ensure that a larger excess of HNO₃ does not arise locally or at any time. This can be effected, for example, by stirring and by appropriate control of the rate of addition.

In general, the use of relatively large amounts of auxiliaries, for example solvents, and cooling and warming of the reaction mixture involve a relatively great technical effort. It is therefore particularly advantageous to carry out the process according to the invention by using commercially available 96% strength sulphuric acid as the solvent and also employing concentrated, approximately 98% strength, nitric acid.

Since the reaction is exothermic, the temperature rises during the reaction and the reaction mixture must be cooled. Advantageously, therefore, the mixture is cooled before the start of the reaction and the temperature is allowed to rise during the reaction. The range between −15 and 10° C has proved to be particularly appropriate.

When the reaction has ended, the reaction mixture is worked up in the customary manner. For example, the sulphuric acid solution can be diluted with water, whereupon the reaction product precipitates out and can be separated from the mother liquor in the customary manner, for example by filtration. Advantageously, as is known, ice or a mixture of water and ice can also be used instead of water in order to dilute the sulphuric acid solution, or the sulphuric acid solution can be poured onto ice or into a mixture of water and ice. In this way, as is known, the warming which arises as a result of the heat of dilution of sulphuric acid is reduced or prevented, so that no further cooling is necessary.

The mother liquor obtained after separating off the reaction product contains only small amounts of excess HNO₃ and organic material if an inert organic solvent has not been used. By means of distillation any inert organic solvent can be separated off easily and the sulphuric acid can be concentrated. Whilst the inert organic solvent and the sulphuric acid can be re-used, so that the process according to the invention is especially suitable for continuous operation also, only the water formed during the reaction remains as the sole waste product. The extent to which the process according to the invention pollutes the environment is therefore particularly small.

The technical advance of the process according to the invention is, in particular, based on the fact that, surprisingly, 4,4′-dinitro-diphenyl carbonate is obtained as the nitration product, in high purity and high yield. According to the state of the art, a purity of at most about 80% was to be expected from quantitative mononitration of either benzene nucleus.

4,4′-Dinitro-diphenyl carbonate is an important intermediate product used in the preparation of, for example, p-nitrophenol, 4,4′-dinitro-diphenyl ether and 4-nitrodiphenylamine, which are industrially important compounds, by known processes.

In the examples which follow, the purity of the 4,4′-dinitro-diphenyl carbonate was in each case determined by quantitative saponification and quantitative analysis of the hydrolysis products.

EXAMPLE 1

107 g (0.5 mol) of diphenyl carbonate are dissolved in one liter of 96% strength by weight sulphuric acid (remainder water) and the solution is cooled to −20° C. 44 ml ( = 1.03 mols of HNO₃) of 98% strength by weight nitric acid (remainder water) are added dropwise in the course of 15 minutes at −20 to −15° C, whilst stirring. The reaction mixture is then stirred for a further 5 minutes at −15° C and then poured onto ice. After the ice has melted, the precipitate which has separated out is filtered off, washed with water and then dried.

In this way 150.6 g (99% of theory) of 4,4′-dinitro-diphenyl carbonate in a purity of 93% are obtained.

Hydrolysis of the resulting 4,4′-dinitro-diphenyl carbonate gave, after working up in a known manner, 132.2 g (95.2% of theory, relative to diphenyl carbonate) of p-nitrophenol.

EXAMPLE 2

107 g of diphenyl carbonate are dissolved in 3 liters of 96% strength by weight sulphuric acid and the solution is cooled to −5° C. 44 ml of 98% strength by weight nitric acid are then added dropwise in the course of 15 minutes at −5° to 0° C and the mixture is stirred for a further 5 minutes at 0° C. The reaction mixture is then discharged onto ice and, finally, the precipitate which has separated out is filtered off, washed with water and dried.

In this way 149.5 g (about 98.5% of theory) of 4,4′-dinitro-diphenyl carbonate in a purity of 90% are obtained.

Hydrolysis of the resulting 4,4′-dinitro-diphenyl carbonate gave, in a known manner, 129.7 g (93.3% of theory, relative to diphenyl carbonate) of p-nitrophenol.

EXAMPLE 3

107 g of diphenyl carbonate are dissolved in 3 liters of 87% strength by weight sulphuric acid and the solution is cooled to 0° C. Subsequently, as described in Example 2, 44 ml of 98% strength by weight nitric acid are added dropwise and the reaction mixture is stirred further and worked up.

In this way 150.2 g (98.8% of theory) of 4,4′-dinitro-diphenyl carbonate in a purity of 79% are obtained.

EXAMPLE 4

The procedure is as in Example 2 but a temperature of 30° C is maintained throughout.

After working up, 149.8 g (98.5% of theory) of 4,4′-dinitro-diphenyl carbonate in a purity of 72% are obtained.

EXAMPLE 5

107 g of diphenyl carbonate are dissolved in one liter of 96% strength by weight sulphuric acid and the solution is cooled to −5° C. Subsequently, as described in Example 2, 98% strength by weight nitric acid is added dropwise and the reaction mixture is stirred further and worked up. 150.0 g (98.6% of theory) of 4,4'-dinitro-diphenyl carbonate in a purity of 75% are obtained.

EXAMPLE 6

107 g of diphenyl carbonate are dissolved in 0.75 l of 96% strength by weight sulphuric acid and the solution is cooled to −5° C. Subsequently, as described in Example 2, 98% strength by weight nitric acid is added dropwise and the reaction mixture is stirred further and worked up.

149.1 g (98.0% of theory) of 4,4'-dinitro-diphenyl carbonate in a purity of 59% are obtained.

EXAMPLE 7

107 g of diphenyl carbonate are dissolved in 1 liter of 96% strength by weight sulphuric acid and the solution is cooled to 0° C. 51 ml (= 1.2 mols) of 98% strength by weight nitric acid are then added dropwise in the course of 15 minutes, at 0°–5° C, whilst stirring. Subsequently, the reaction mixture is stirred for a further 5 minutes at 0° C and then worked up as described in Example 2.

In this way 149.8 g (98.5% of theory) of 4,4'-dinitro-diphenyl carbonate in a purity of 74% are obtained.

EXAMPLE 8

107 g of diphenyl carbonate are dissolved in 1 l of 100% strength by weight sulphuric acid and the solution is cooled to −5° C. Subsequently, as described in Example 2, 98% strength by weight nitric acid is added dropwise and the reaction mixture is stirred further and then worked up. In this way 149.0 g (98.0% of theory) of 4,4'-dinitro-diphenyl carbonate in a purity of 76% are obtained.

EXAMPLE 9

107 g of diphenyl carbonate are dissolved in 1 l of 85% strength by weight sulphuric acid and the solution is cooled to −5° C. Subsequently, as described in Example 2, 98% strength by weight nitric acid is added dropwise and the reaction mixture is stirred further and then worked up.

149.5 g (98.5% of theory) of 4,4'-dinitro-diphenyl carbonate in a purity of 73% are obtained.

EXAMPLE 10

107 g of diphenyl carbonate are dissolved in a mixture of 500 ml of 100% strength by weight sulphuric acid and 500 ml of methylene chloride and subsequently 44 ml of 98% strength by weight nitric acid are added in the course of about 15 minutes, in the temperature range from 15° to 20° C, whilst stirring. The reaction mixture is stirred for a further 5 minutes at 20° C and discharged onto ice. After the ice has melted, the organic phase is separated off and the aqueous phase is extracted several times by shaking with methylene chloride. The combined methylene chloride solutions are washed several times with water and then concentrated to dryness in a rotary evaporator.

In this way 148 g (about 98% of theory) of 4,4'-dinitro-diphenyl carbonate in a purity of 87% are obtained.

Hydrolysis of the resulting 4,4'-dinitro-diphenyl carbonate in a known manner gave 126.5 g (90.9% of theory, relative to diphenyl carbonate) of p-nitrophenol.

EXAMPLE 11

107 g of diphenyl carbonate are dissolved in a mixture of one liter of 96% strength by weight sulphuric acid and 200 ml of acetic acid. 44 ml of 98% strength nitric acid are added dropwise in the course of 15 minutes, at about 0° C, to the solution, which has been cooled to the same temperature, whilst stirring. The reaction mixture is then stirred for a further 5 minutes and poured onto ice. After the ice has melted, the precipitate which has separated out is filtered off, washed with water and dried.

In this way 149 g (about 98% of theory) of 4,4'-dinitro-diphenyl carbonate in a purity of 84% are obtained.

Hydrolysis of the resulting 4,4'-dinitro-diphenyl carbonate in a known manner gave 125.0 g (89.8% of theory, relative to diphenyl carbonate) of p-nitrophenol.

What is claimed is:

1. A process for the preparation of 4,4'-dinitro-diphenyl carbonate which comprises adding to a sulfuric acid solution of diphenyl carbonate maintained at a temperature between −40 and +40° C a stoichiometric or slightly stoichiometric excess of nitric acid relative to said diphenyl carbonate, the sulfuric acid having a strength of 80–100 percent and the concentration of diphenyl carbonate in the sulfuric acid being between 2 and 40 percent by weight based upon the volume of sulfuric acid.

2. A process according to claim 1 wherein the nitric acid is present in a stoichiometric excess up to a 10% stoichiometric excess.

3. A process according to claim 1 wherein the nitric acid is added to a mixture of sulfuric acid and inert organic solvent.

4. A process according to claim 1 wherein the process is carried out in the temperature range of −20 to +30° C.

5. A process according to claim 1 wherein the nitric acid employed is in a strength of 65 to 98%.

6. A process according to claim 3 wherein the inert organic solvent is selected from the group consisting of halogen alkanes, aromatic nitrohydrocarbons, lower aliphatic carboxylic acids and lower aliphatic carboxylic acid anhydrides.

7. A process according to claim 6 wherein the aromatic solvent is selected from the group consisting of methylene chloride, carbon tetrachloride, dichloroethane, nitrobenzene, nitrotoluene, formic acid, acetic acid, propionic acid and acetic anhydride.

8. A process according to claim 6 wherein the volume ratio of inert organic solvent to sulfuric acid is in the range of 1:30 to 30:1.

* * * * *